US008246908B2

(12) United States Patent
Kajiyama et al.

(10) Patent No.: US 8,246,908 B2
(45) Date of Patent: Aug. 21, 2012

(54) SMALL SIZE GENE ANALYSIS APPARATUS

(75) Inventors: Tomoharu Kajiyama, Higashiyamato (JP); Hideki Kambara, Hachioji (JP); Kunio Harada, Hachioji (JP)

(73) Assignee: Hitachi Ltd., Tokyo (JP)

( * ) Notice: Subject to any disclaimer, the term of this patent is extended or adjusted under 35 U.S.C. 154(b) by 246 days.

(21) Appl. No.: 11/708,316

(22) Filed: Feb. 21, 2007

(65) Prior Publication Data

US 2009/0087344 A1  Apr. 2, 2009

Related U.S. Application Data

(62) Division of application No. 11/601,725, filed on Nov. 20, 2006.

(30) Foreign Application Priority Data

Nov. 28, 2005 (JP) .................................. 2005-341367

(51) Int. Cl.
*G01N 21/00* (2006.01)

(52) U.S. Cl. ................ 422/65; 422/63; 422/64; 422/50; 422/500; 422/501; 422/502; 436/180

(58) Field of Classification Search .............. 422/63–67, 422/99–100, 50, 500–502; 73/863.32; 436/180
See application file for complete search history.

(56) References Cited

U.S. PATENT DOCUMENTS

| 3,508,878 | A | * | 4/1970 | Gunders ........................... 422/73 |
| 4,276,048 | A | * | 6/1981 | Leaback ......................... 436/180 |
| 4,451,433 | A |   | 5/1984 | Yamashita et al. |
| 5,391,352 | A | * | 2/1995 | Hendrix et al. ................... 422/65 |
| 5,460,779 | A | * | 10/1995 | Kratzer et al. ................... 422/73 |
| 5,547,849 | A | * | 8/1996 | Baer et al. ..................... 435/7.24 |
| 5,943,075 | A |   | 8/1999 | Lee et al. |
| 6,104,485 | A | * | 8/2000 | Wang et al. ................... 356/246 |
| 6,319,469 | B1 | * | 11/2001 | Mian et al. ....................... 422/64 |
| 6,521,187 | B1 |   | 2/2003 | Papen |
| 6,673,532 | B2 |   | 1/2004 | Rao |
| 6,864,480 | B2 | * | 3/2005 | Staats ............................. 506/33 |
| 2001/0024790 | A1 |   | 9/2001 | Kambara et al. |
| 2002/0003177 | A1 |   | 1/2002 | O'Connor et al. |
| 2003/0086823 | A1 |   | 5/2003 | Fernando et al. |

FOREIGN PATENT DOCUMENTS

| JP | 09-234099 | 3/1996 |
| JP | 09-234099 | 9/1997 |
| JP | 2001-258543 | 3/2000 |

(Continued)

OTHER PUBLICATIONS

Search Report from European Patent Office dated Mar. 16, 2007.

(Continued)

*Primary Examiner* — Jyoti Nagpaul
(74) *Attorney, Agent, or Firm* — Stites & Harbison, PLLC; Juan Carlos A. Marquez, Esq (57) ABSTRACT

By the conventional technique for dispensing more than one reagents accurately, the system is complicated and thus a compact and inexpensive system is difficult to realize. In the present invention, the pressurized dispensing system utilizing a capillary is realized, and in addition, in order to reduce the leakage of reagents different from the reagent dispensed, by forming air layers at the tips of the capillaries after dispensing, a compact, simple, inexpensive analysis apparatus is realized.

13 Claims, 9 Drawing Sheets

FOREIGN PATENT DOCUMENTS

| | | |
|---|---|---|
| JP | 2001-258543 | 9/2001 |
| JP | 2001-258543 | 9/2001 |
| JP | 2004-012411 | 6/2002 |
| JP | 2004-012411 | 11/2002 |
| JP | 2003-098172 | 4/2003 |
| JP | 2004-012411 | 1/2004 |
| JP | 2004-0122411 | 1/2004 |
| JP | 2004-093440 | 3/2004 |
| WO | WO 98/13523 | 9/1997 |
| WO | WO 98/28440 | 12/1997 |
| WO | WO 98/13523 | 4/1998 |
| WO | WO 98/28440 | 7/1998 |
| WO | WO 00/56455 | 3/2000 |
| WO | WO 00/56455 | 9/2000 |
| WO | WO 01/77640 A2 | 4/2001 |
| WO | WO 01/77640 A2 | 10/2001 |
| WO | WO 02/081088 A2 | 3/2002 |
| WO | WO 02/081088 A2 | 10/2002 |
| WO | WO 03/050231 A1 | 12/2002 |
| WO | WO 03/050231 A1 | 6/2003 |
| WO | WO 2004/076018 A2 | 2/2004 |
| WO | WO 2004/076018 A2 | 9/2004 |

OTHER PUBLICATIONS

Office Action from the Chinese Patent Office dated Mar. 16, 2007.
Office Action for U.S. Appl. No. 11/601,725 dated Sep. 4, 2009.
European Search Report of EP Application No. 06023582.07-2113 dated Mar. 16, 2007.
Office Action from U.S. Appl. No. 11/601,725 mailed May 5, 2010.
Office Action mailed Feb. 22, 2011 in the U.S. Appl. No. 11/601,725.
"HemataSTAT® Frequently Asked Questions", © 2010 Thermo Fisher Scientific Inc., http://www.separationtechnoloqy.com/hemetastat_faq.html (2 pages).
Charles Riva, et al., "Laser Doppler measurements of blood flow in capillary tubes and retinal arteries", Invest. Ophthalmol. Vis. Sci. Nov. 1972, vol. 11, No. 11, pp. 936-944.

* cited by examiner

SMALL SIZE GENE ANALYSIS APPARATUS

CROSS-REFERENCE TO RELATED APPLICATION

This application is a Divisional application of U.S. application Ser. No. 11/601,725 filed Nov. 20, 2006. Priority is claimed based on U.S. application Ser. No. 11/601,725 filed Nov. 20, 2006, which claims the priority of Japanese Patent Application No. 2005-341367 filed on Nov. 28, 2005, all of which is incorporated by reference.

BACKGROUND OF THE INVENTION (1) Field of the Invention

The present invention relates to an apparatus analyzing nucleic acids, and in particular, an apparatus capable of analyzing gene sequences, gene polymorphism, and gene mutation.

(2) Description of Related Art

For determining DNA base sequences, methods using gel electrophoresis and fluorescence detection are widely used. In such method, first, many copies of a DNA fragment are made, the sequence of which is to be analyzed. Fluorescence-labeled fragments of various lengths are prepared, 5'-terminals of the DNA being starting points, wherein fluorescent labels are also attached, wavelengths varying with bases at 3'-terminals of these DNA fragments. The difference in length is identified by one base by gel electrophoresis, and emission from each of the fragment groups is detected. DNA terminal base types of the DNA fragment groups being studied are elucidated according to colors of emission wavelengths. The DNA fragment groups pass through the fluorescent detection section one by one from a shorter one, so that terminal base types can be identified consecutively from a shorter DNA by measuring fluorescence colors. Thereby, the sequence is determined. Such fluorescent DNA sequencers are widespread, and also their contribution to the Human Genome Project was enormous. On the other hand, the Human Genome Project was completed, as declared in 2003, and the time has come to make use of sequence information in medicine and various industries. There, in many cases, analysis of entire long DNA is not required and elucidation of a short DNA sequence of interest is sufficient. For such DNA sequence analysis, simple methods and apparatuses are required.

The sequence determination by stepwise chemical reactions such as pyrosequencing is a technique developed in order to meet such requirement (for example, Patent document 1 and Patent document 2). In this method, a primer is hybridized with a target DNA strand, and four nucleic acid substrates for complementary strand synthesis (dATP, dCTP, dGTP, and dTTP) are added one by one in order into the reaction solution, and thereby a complementary strand is synthesized. Upon complementary strand synthesis, as the complementary DNA strand extends, pyrophosphate (PPi) is generated as a by-product. In the presence of an enzyme, pyrophosphate is converted to ATP, which in turn goes through the reaction in the presence of luciferin and luciferase to generate emission. By detecting this emission, the incorporation of the nucleic acid substrates for complementary strand synthesis in the DNA strand is confirmed, and the sequence information of the complementary strand, and consequently the sequence information of the target DNA strand will be elucidated. On the other hand, the nucleic acid substrates for complementary strand synthesis that have not been used in the reaction are promptly degraded by an enzyme such as apyrase so as not to interfere with subsequent reaction steps (for example, Patent document 2). Many apparatuses for this pyrosequencing employ chemiluminescent detection system, wherein a titer plate having 96 reaction cells (having a volume of 100 µl or less) is utilized as a reaction cell plate. In such apparatus, each of the four nucleic acid substrates for complementary strand synthesis (dATP, dCTP, dGTP, and dTTP) is contained in a separate reagent vessel and injected into the reaction cells one by one (for example, Patent document 3). That is, DNA, a primer, enzymes for synthesizing a complementary strand, chemiluminescent reagents, and the like are placed in advance in the reaction cells; a reagent dispenser comprises four nozzles; the nozzles or a titer plate is moved in the x-y directions as well as in the rotation direction; the air in the reagent vessels is pressurized; and thereby the reagents are dripped one by one from the tips of the nozzles, thus emission being detected.

Furthermore, a technology to provide a small size apparatus for the above pyrosequencing is disclosed (for example, Patent document 4). In this technology, a narrow tube is connected from each of dNTP vessels to the reaction section; it is suggested that compact and simple analysis is attainable by the method wherein four dNTPs are injected one by one by using these narrow tubes.

On the other hand, a luminescence detection apparatus utilizing a pressurized dispensing system for dispensing reagents is disclosed as a small size apparatus for measuring bioluminescence (for example, Patent document 5). In this technology, capillaries for dispensing are aligned with reaction cells one by one, and dispensing reagents is controlled by pressurization.

Moreover, in regarding to reagents that can be used for the pyrosequencing reaction, an example of a reaction system different from the technologies described above is disclosed (for example, Patent document 6). In this conventional technology, AMP and PPi are synthesized into ATP by using the reverse reaction of the enzyme, pyruvate, phosphate dikinase (PPDK), and AMP concentrations are measured.

Patent document 1: WO 98/13523
Patent document 2: WO 98/28440
Patent document 3: WO 00/56455
Patent document 4: JP-A-2001-258543
Patent document 5: JP-A-2004-12411
Patent document 6: JP-A-9-234099

It is believed that because the reaction mechanism used is simple, the pyrosequencing method is suitable for small size and inexpensive apparatuses. Four nucleic acid substrates for complementary strand synthesis are required for measurement, as described above, and hence these need to be measured accurately. In order to make an apparatus small and inexpensive, it is also essential to design to use a minute total amount of reagents.

In the conventional technology, there is a problem that an accurate reagent dispensing mechanism can not be small and inexpensive. For example, in order to make an apparatus small, dispensing about 0.1 to 0.2 µl needs to be performed within an error of 10% or less. However, conventionally, in the method of dripping reagents, which is said to be a simple method of dispensing reagents, for example, on dispensing 0.4 µl, a dispensing error of about 15% occurs, and on dispensing less than 0.4 µl, in many cases, dispensing is not possible due to surface tension of the liquid. Furthermore, another example to realize micro-dispensing is the Bubble Jet® technology, in general, used for inkjet printers, which has problems such that reagents are deteriorated by heating and that it is difficult to simplify replenishment and maintenance. Moreover, in the pressurized dispenser method using capillaries, which can realize simple, inexpensive, accurate dispensing, nevertheless, because the tip of the capillary is in contact with a sample solution in the reaction vessel, reagents may disadvantageously leak at the time the air is not pressurized.

Furthermore, four reagents need to be injected into a reaction vessel in a predetermined order. In the conventional nozzle method, there are problems that miniaturization is difficult and parallel arrangement is also difficult. That is, in a 96-well titer plate widely used in this field, 96 reaction vessels (holes) are placed with a pitch of 9 mm, but it is impossible to provide a plurality of nozzles with a pitch of 9 mm by the conventional technology. Therefore, the reagents are dispensed through a set of nozzles into multiple reaction vessels, so that the measurement efficiency is low as well as the horizontal mechanism movement tends to be large and expensive.

Furthermore, the mechanism that allows the dispensed substrates to admix with a sample in the reaction vessel efficiently is required. In order to realize a simple, small size, inexpensive apparatus, these problems should be solved.

SUMMARY OF THE INVENTION

In order to solve the problems described above, a single-piece dispensing chip having four reagent containing spaces has been invented in the present invention. This chip employs a pressurized dispensing system utilizing capillaries and having a high dispensing accuracy. In order to realize placement with a pitch of 9 mm, the chip is miniaturized, and will be attached to the head so that replenishment of the reagents, etc. can be simplified. The chip is disposable, designed to be used up.

Furthermore, a vertical movement mechanism is provided on the head part holding the chip. Thereby, whether the capillary and the liquid in the reaction cell are in contact or not can be controlled at the time of reagent dispensing and at the time of stirring. Furthermore, an air gap is provided in the capillary. Thereby, a reagent is kept from leaking from the tip of the capillary of the chip. As compact and simple means of forming an air gap, a microejector utilizing a high pressure gas (such as air or nitrogen) operated by the pressurized dispensing system is provided, and the negative pressure generated thereby is utilized. Consequently, the formation of an air gap can be reliable.

An example of the analysis apparatus in accordance with the present invention is characterized in that the analysis apparatus comprises: reagent container-holding means for holding a reagent container containing a reagent; moving means for moving the reagent container-holding means vertically; a reaction vessel for receiving a supply of the reagent from the reagent container and containing the liquid; pressurizing means for applying pressure to the reagent container to supply the reagent therefrom to the reaction vessel; vibrating means for applying vibration to the reaction vessel; and a detector for optical detection for the reaction vessel.

Another example of the analysis apparatus in accordance with the present invention is characterized in that the analysis apparatus comprises: reagent container-holding means for holding a reagent container comprising a reagent delivering part and containing a reagent; moving means for moving the reagent container-holding means vertically; a reaction vessel for receiving a supply of the reagent from the reagent container and containing a sample; pressurizing means for applying pressure to the reagent container to supply the reagent therefrom to the reaction vessel; vibrating means for applying vibration to the reaction vessel; a detector for optical detection for the reaction vessel; and a negative pressure-generating mean for providing an air layer inside the reagent delivering part.

An example of the reagent kit in accordance with the present invention is characterized in that the kit includes: a first vessel, which comprises a first liquid delivering part and contains a first liquid; a second vessel, which comprises a second liquid delivering part and contains a second liquid; a third vessel, which comprises a third liquid delivering part and contains a third liquid; and a fourth vessel, which comprises a fourth liquid delivering part and contains a fourth liquid, and that the first liquid delivering part, the second liquid delivering part, the third liquid delivering part, and the fourth liquid delivering part are essentially placed being symmetric with respect to a point.

The present invention can realize a small size and inexpensive apparatus that analyzes nucleic acids and gene sequences. First, by the method in accordance with the present invention, dispensing chips as many as desired can be inexpensively arranged in parallel. Furthermore, desired dispensing accuracy can be attained in a compact and simple manner. In addition, replenishment of the reagents, etc., is easy. Moreover, the present method is suitable for admixing of the reagent that determines reaction efficiency. Thereby, sequence analysis can be performed with high accuracy. Furthermore, by preventing a pressurized dispensing system utilizing capillaries from leaking a reagent, accuracy of the reaction can be improved.

Other objects, features and advantages of the invention will become apparent from the following description of the embodiments of the invention taken in conjunction with the accompanying drawings.

BRIEF DESCRIPTION OF THE SEVERAL VIEWS OF THE DRAWING

FIGS. 3(1), 3(2), and 3(3) are illustrations to explain the dispensing head into which the chips are inserted;

DETAILED DESCRIPTION OF THE INVENTION

Embodiment 1

Now, the present invention will be described referring to Embodiments.

Figure 1A:
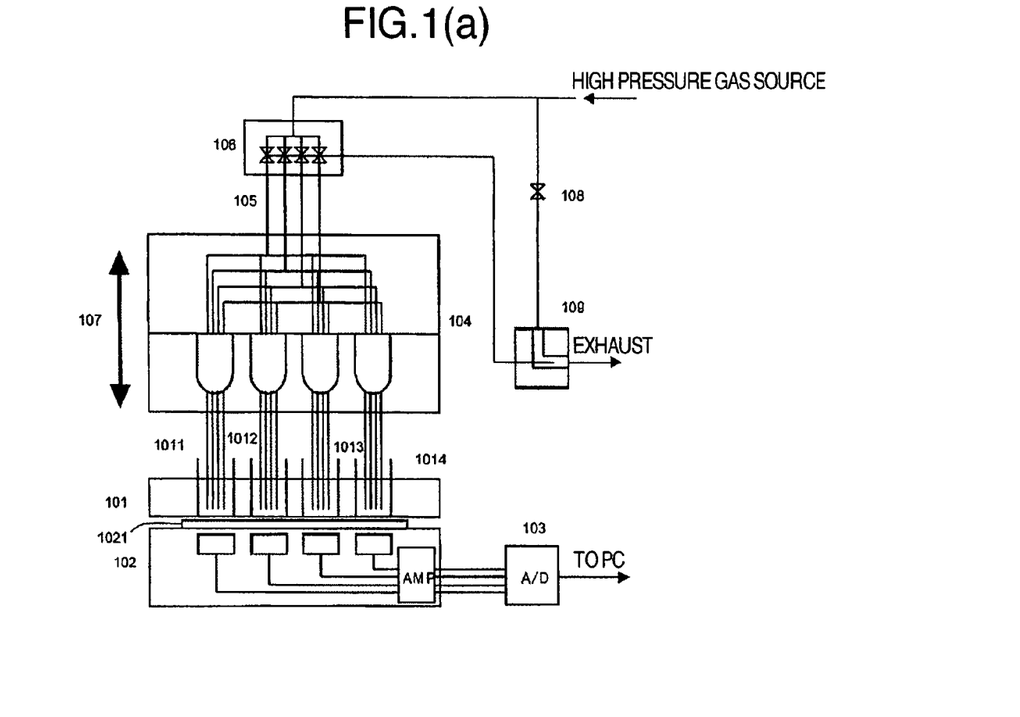
FIGS. 1(a) and 1(b) illustrate examples of the configuration of the apparatus.

In the present invention, the target gene sequence to measure is determined by using the principle of the pyrosequencing method described in the Description of Related Art section. First, an example of the configuration of the apparatus for analysis according to the present invention is shown in FIG. 1(a). First, the apparatus has a reaction vessel holder 101. The holder 101 supports four reaction vessels 1011 to 1014 in a single row with a pitch of 9 mm. The present apparatus performs nucleic acid extension using enzymes, and enzymatic reactions, in general, work efficiently when the temperature is higher than room temperature, so that it is more preferable that temperature controlling means (such as a peltier element), by which heating or cooling to a given temperature can be conducted, is connected to the holder. In addition, in this embodiment, four reaction vessels are placed with a pitch of 9 mm (a pitch of a 96-hole titer plate), but any number of reaction vessels and any pitch can be given in applications and the number of reaction vessels and the pitch size are not limited. Moreover, the total number of reaction vessels can be increased by providing more than one row shown in FIG. 1. The holder 101 can be vibrated in its entirety by a vibration generating device such as a vibration motor. Such vibration is useful for admixing dispensed reagents and a sample in a reaction vessel upon dispensing reagents.

A light detection part 102 is covered in its entirety by a casing made of an electrically conductive material, having four photodiodes facing toward the reaction vessels in alignment with the pitch of the reaction vessels. The interface with the reaction vessels has a glass 1021 having a transparent electrode layer (ITO, etc.) at the back. This transparent electrode is electrically connected to the electrically conductive casing covering the entirety, and is connected to ground potential of the apparatus. In addition, inside the casing, an amplifier that amplifies signals from the photodiodes is included, the amplifier connecting to an A/D conversion circuit outside the detection part.

The A/D conversion circuit 103 digitizes light detection signals and transmits data to a computer for controlling the apparatus and for receiving the data.

Figure 1B:
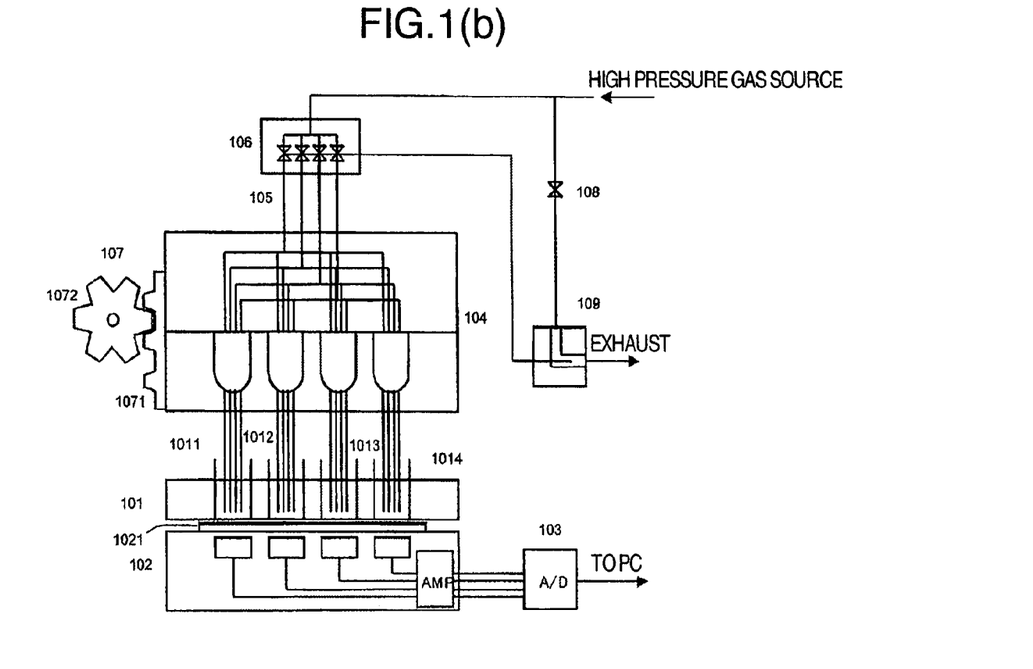

A dispensing head 104 has a function as means of holding dispensing chips, by which dispensing chips are held therein. Herein, the chip comprises capillaries for dispensing, the chip being held in a manner that the end of the capillary for dispensing opposes the reaction vessel. Furthermore, a group of four air tubes for pressurization 105, each of which corresponds to one of four reagents, respectively, are connected to a group of solenoid valves 106. However, the dispensing head and the group of solenoid valves may be made as a single piece. In addition, a mechanism for moving up and down 107 the entirety of the dispensing head is included. In regard to the vertical movement mechanism 107, for example, it is easy to provide a rack 1071 to the head 104 and drive a pinion 1072 by a motor, etc., as shown in FIG. 1(b). In such case, the vertical position of the head can be controlled with a contact switch or by the number of revolution of the motor. Moreover, the effects that can be obtained when the vertical position can be controlled will be described later. To put it simply, it is also possible to move the head up and down by using a syringe that utilizes gas provided from a high pressure gas source. Such method is simple, because controlling up and down movements is attained by filling the gas with the use of a single solenoid valve.

The group of solenoid valves have four 3-way solenoid valves, and its side of a high pressure gas source is connected to a high pressure gas tank included in the apparatus or a high pressure gas line source provided in a laboratory. Furthermore, its exhaust side is connected via another solenoid valve 108 to a microejector, which is a negative pressure source 109. The negative pressure source 109 uses the microejector and the high pressure gas source to generate negative pressure of about 0.5 atm. The generation of negative pressure is controlled by the solenoid valve 108.

Figure 2:
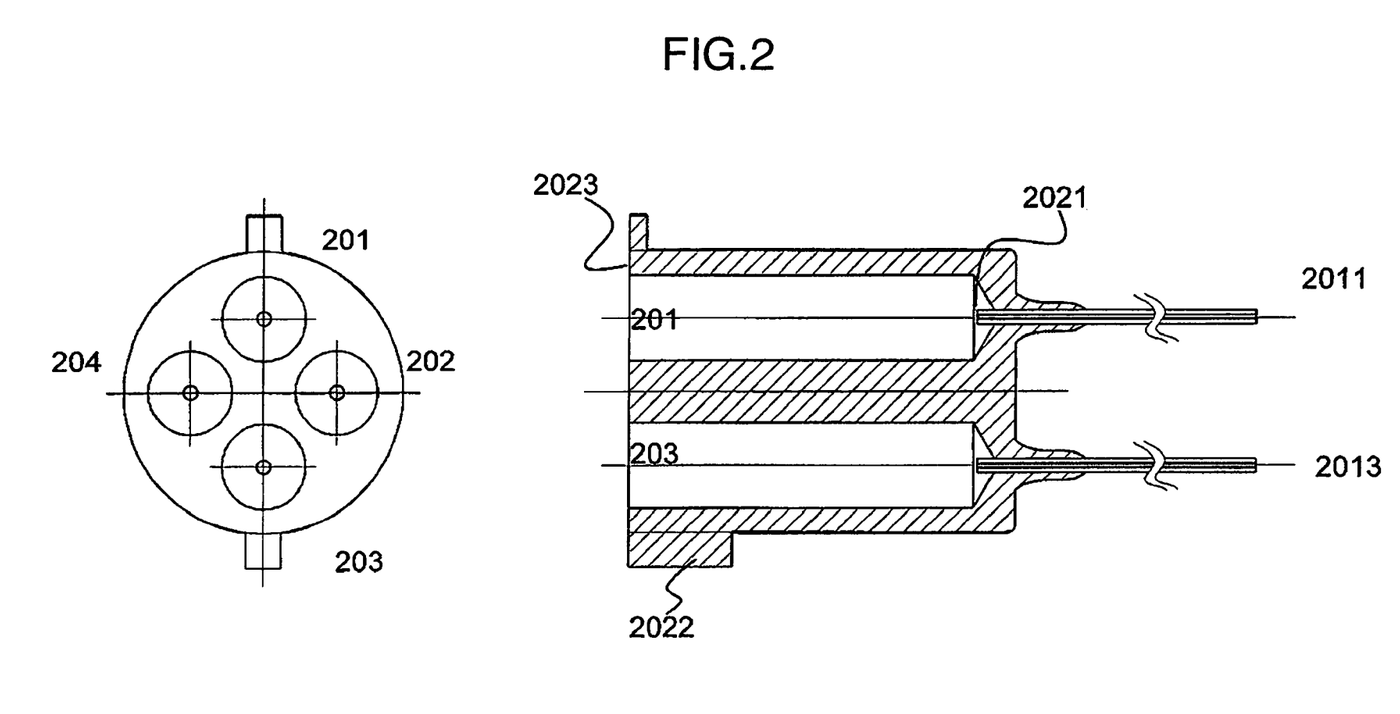
FIG. 2 illustrates the dispensing chip.
Figure 3:
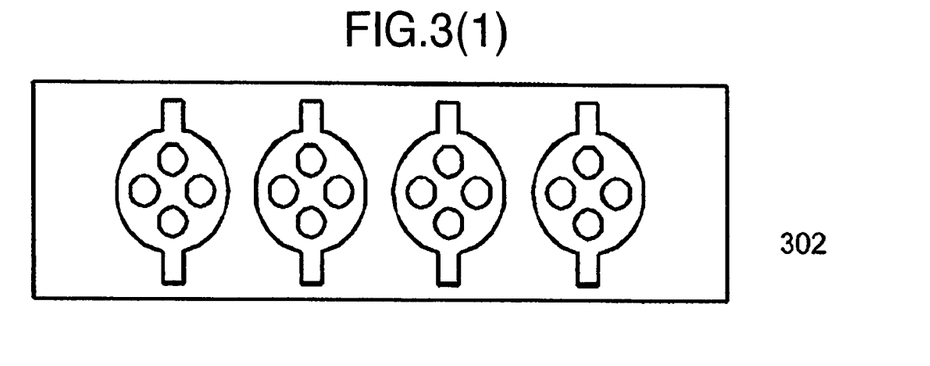

A top view and a sectional view of the dispensing chip are shown in FIG. 2. The dispensing chip includes reagent vessels 201 to 204 containing each of four reagents, respectively. Each of the reagent vessels includes a capillary 2011 to 2014, respectively, the capillary being a dispensing path. In this embodiment, a glass capillary, the total length being 20 mm, the outer diameter being about 350 μm, and the inner diameter being about 50 μm, is used as a capillary. The inner diameter and the length of a reagent vessel are 2.4 mm and 10 mm, respectively. The volume of a reagent vessel is about 45 μL. Four reagents contained in the reagent vessels are expected to be deoxynucleotide triphosphates (dNTPs), for example. Particularly, in each of the four reagent vessels, deoxyadenosine triphosphate (dATP), deoxythymidine triphosphate (dTTP), deoxycytidine triphosphate (dCTP), and deoxyguanosine triphosphate (dGTP) are expected to be contained. Moreover, analogues of dNTPs may also be used. For example, in place of triphosphate, dNTPαS, wherein one phosphorus at the α-position is substituted with a sulfur, and the like may be used.

In the dispensing chip, the four reagent vessels are essentially placed being symmetric with respect to a point, so that the location where each reagent is dispensed is equally placed from the center. There are the following advantages. First, by coinciding the center of the dispensing chip with the center of the reaction vessel, no location difference arises among the four reagents. That is, the location in the reaction vessel of a capillary is closely related to the degree of admixing of a reagent after dispensing. The reaction vessel is a cylinder, and hence the ideal location for dispensing is the center of the reaction vessel, when the effect of admixing a reagent is considered. However, when the four reagents are dispensed as a package, and if all are to be at the center, a horizontal mechanism movement and the like are required, resulting in an increase in cost of the apparatus. Therefore, in order to handle the four reagents equally, the placement that is essentially concentrical from the center of a reaction vessel is most suitable.

Furthermore, the bottom of the reagent vessel, i.e., the connection part with the capillary, has essentially a conical shape (2021), the center residing at the location where the capillary is placed. Thereby, the amount of a reagent which becomes undispensable, i.e., the dead volume can be minimized. Moreover, the dispensing chip itself is symmetric with respect to a line, and it is convenient to provide a pin for positioning 2022 in order not to misplace the four reagents. Moreover, the end of the top of the chip 2023 is designed to be essentially on the same plane. Thereby, it is advantageously easy to secure airtightly the chips in a chip holder by airtight members 3001 to 3004, which will be described later. Likewise, it is also easy to apply to the top a lid for sealing or a sealing agent so as to prevent the reagents from drying.

Furthermore, this chip itself is a cylinder having a diameter of less than 9 mm, and hence it can be effectively placed at the titer plate's pitch.

FIG. 3 is a schematic illustration of the dispensing head. (1) is a bottom view of the top of the dispensing head, (2) is a sectional view of the head, and (3) is a top view of the bottom of the dispensing head. The dispensing head is assembled in a manner that the bottom of (1) and the top of (3) are joined. More particularly, the dispensing head can be separated into the bottom 301 of the dispensing head and the top 302 of the dispensing head, the dispensing chip shown in FIG. 2 is inserted therebetween. To the bottom of the dispensing head, a hole to allow the capillaries of each dispensing chip to go through is provided. To the top of the dispensing head, four high pressure gas flow entrances per chip, which are individually connected to each of the reagent vessels of the chip, are provided. The part 303 refers to one of high pressure gas flow paths. One flow path of the high pressure gas corresponds to one reagent vessel, and is connected to the gas flow entrance of each dispensing chip. The flow paths gather into one, which is connected to one air tube. The airtight members 3001 to 3004, being in tight contact with the chips, can keep each reagent vessel in an airtight condition. For a member most suitable to provide air tightness, materials having rubber elasticity such as silicone rubber and Viton® rubber are suitable.

First, characteristics of the dispensing chip and others in accordance with the present invention are described. The pressurized dispensing system utilizing capillaries is characterized by high dispensing accuracy on microdispensing. For example, in this embodiment, a dispensing error of about no more than 10% was attained on dispensing at a dispensing volume of 0.2 µl. Furthermore, with smaller capillaries than the one having an inner diameter of 25 µm in this embodiment, a dispensing error was no more than 8%. Here, the effect that can be obtained by using narrow tubes (capillaries) is described. In the dispensing method in accordance with the present invention, the volume Q of the reagent dispensed is determined by the pressure applied from outside and the duration of pressurization according to the following Hagen-Poiseuille law.

$$Q = \Delta P \cdot \pi \cdot r^4 \cdot t / (8 \mu L)$$

wherein ΔP is the pressure, r is the radius of a capillary, t is the duration of pressurization, µ is the viscosity of a solution, and L is the length of a capillary.

Figure 7:
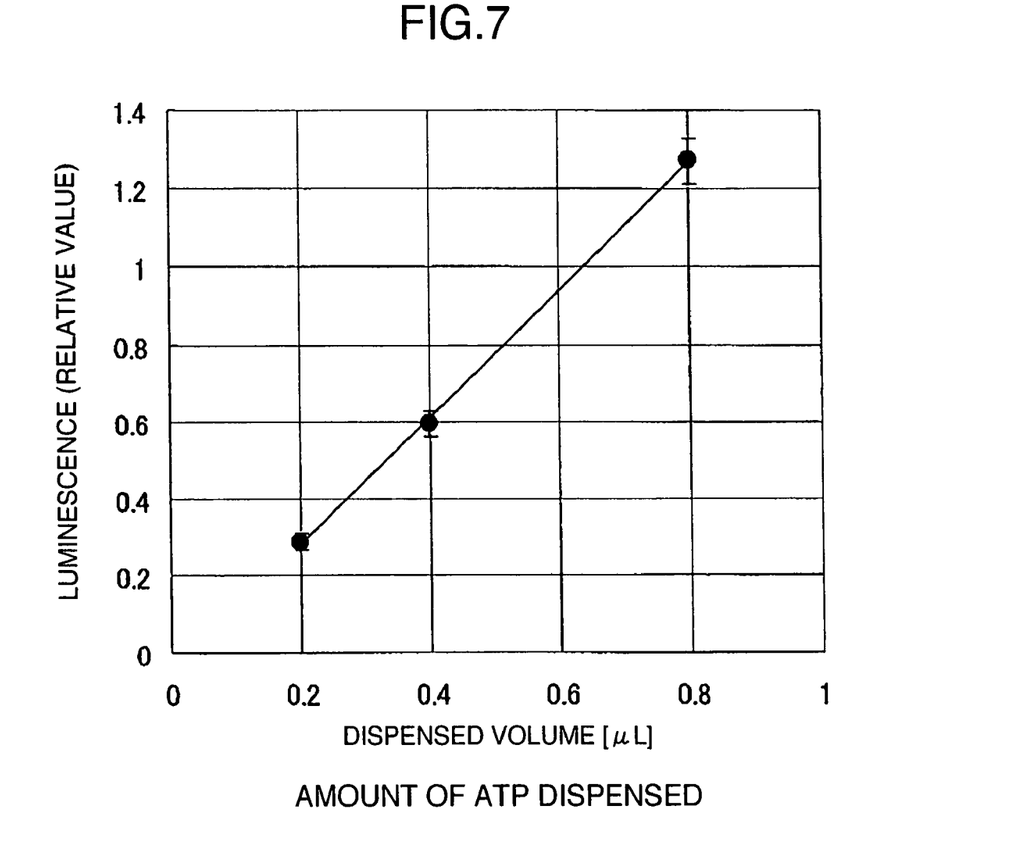
FIG. 7 graphically shows a relation between the amount of ATP dispensed and the level of luminescence.

Dispensing accuracy depends on controllable mechanisms, and hence in this case evaluations of an error of the pressure applied and an error of the duration of pressurization are important. As shown in the above equation, when these errors are the same, the error of the dispensed volume caused by such errors is proportional to the fourth power of the radius of a capillary, and is inversely proportional to the length of a capillary. Therefore, the smaller the radius, the smaller the influence of the error of the pressure applied and the error of the duration of pressurization on the dispensing error. In this embodiment, capillaries in the range of from 50 µm to 25 µm (inclusive) in diameter are used. Capillaries having a diameter of about 1 to 25 µm may be used but tend to be clogged depending on reagents to be dispensed. On the other hand, with capillaries having a diameter of more than 50 µm, as described above, dispensing accuracy is deteriorated. The capillary diameter for use can be selected, as needed, according to a dispensing volume in the mode in use and required accuracy, but under the conditions in this embodiment wherein a dispensing volume and clogs are considered, capillaries having a diameter of from 25 to 50 µm (inclusive) are suitable. A dispensed volume was determined from a change of mass between before and after dispensing, and the error from this was close to the measurement limit. Furthermore, in this system, by allowing the tips of the capillaries to be kept in contact with the liquid in the reaction vessel even when dispensing is not performed, the vertical movement mechanism 107 could be eliminated. However, when the tips of the capillaries are kept in contact with the liquid in the reaction vessel, reagent leakage, which should be avoided, from the tips of the capillaries is anticipated. That is, in ordinary use, the inside of a capillary is filled with a reagent. In this apparatus, it is necessary to dispense any of the four reagents in any volume on nucleic acid analysis, and hence unexpected leak of a reagent into the reaction vessel causes an unexpected reaction to occur, resulting in a serious measurement error. Therefore, the volume of leakage by diffusion of a reagent in this apparatus was evaluated below. The evaluation was performed by using bioluminescent reagents. First, into a reaction vessel, bioluminescent reagents, luciferase and luciferin, having been dissolved in a buffer were added, and into a capillary, ATP was added as a reagent. As shown in FIG. 7, the level of luminescence to the amount of ATP dispensed is linear and known. Thus, an amount of leakage of ATP can be evaluated by measuring weak luminescence, when dispensing is not performed, i.e., the high pressure gas is not injected, the capillary being set as it is.

Figure 8A:
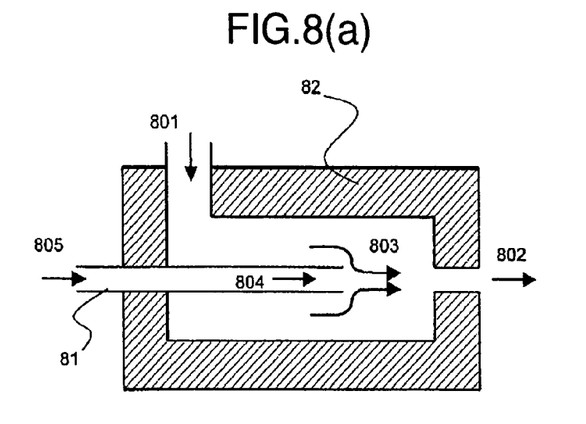
FIGS. 8(a) and 8(b) illustrate a microejector and an example of the configuration of the apparatus including the microejector, respectively.
Figure 8B:
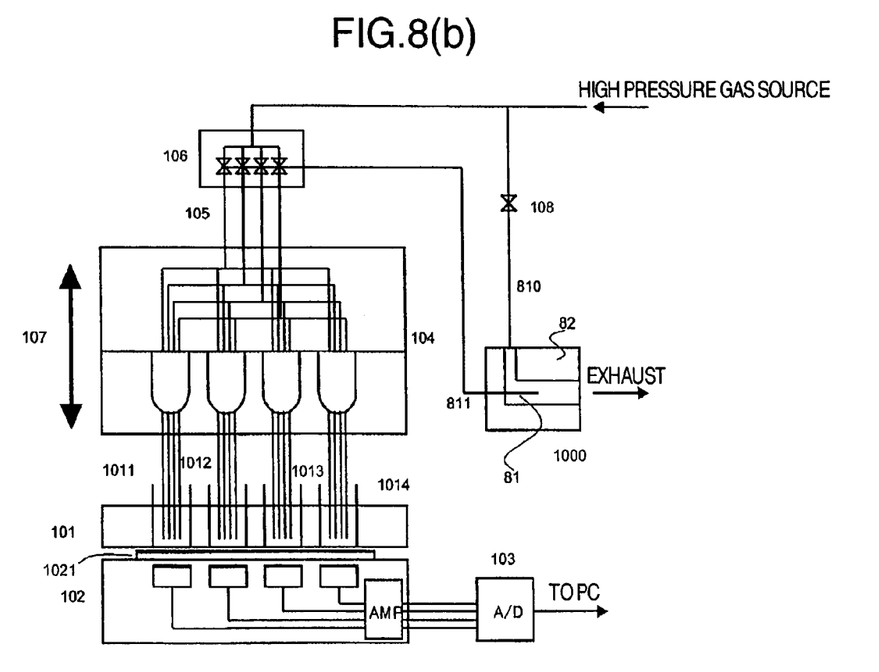

First, the reaction vessel was kept still, and the volume of leakage for two min was measured, but no leakage was observed. On the other hand, in order to stir the reagent, the reaction vessel was vibrated by a vibration generating device for 20 sec, and a large amount of leakage was observed. That is, when the reagent was stirred, it was found that it is important to separate the tip of the capillary from the reagent before stirring. However, in case that the vertical movement mechanism was used, when the tip of the capillary was inserted back again into the liquid in the reaction vessel, reagent leakage that may be caused by the impact thereof was observed. For example, with a capillary having an inner diameter of 50 µm, by the impact arising when the tip was inserted into the surface of the liquid in the reaction vessel, reagent leakage of about 6 nL was observed. And, likewise, with a capillary having an inner diameter of 25 µm, reagent leakage of about 3 nL was observed. These problems can be solved in a manner that after dispensing the reagent, the tip of the capillary is separated from the surface of the liquid, and then a layer of gas (air in this case), i.e., the air gap, is formed at the tip of the capillary (the end where liquid is released). This is because the presence of the layer of gas causes the location of the boundary of the reagent inside the capillary to retract by about 5 mm, so that accidental leakage from the tip of the capillary can be avoided. The air gap, in general, can be formed by sucking the reagent vessel using a syringe. However, when a syringe is used, disadvantages arise because the system becomes costly and complicated including the mechanism related to the syringe. Therefore, in this embodiment, in order to provide a simpler method, negative pressure by using a microejector is utilized. A microejector, as shown in a sectional view of FIG. 8(a), is means of generating negative pressure that comprises a narrow tube 81 and a housing 82 linked to the high pressure gas source. When the high pressure gas flows into the microejector from a flow entrance 801 to an exhaust slot 802, a flow like 803 occurs in the vicinity of the narrow tube residing inside, and thereby the air inside the narrow tube is retracted in the direction of 804, resulting in the generation of negative pressure in the direction of 805. This apparatus already includes the high pressure gas source, and hence by using the microejector, negative pressure can be readily obtained. The reagent vessel is connected to the microejector for very short duration and thereby negative pressure is applied to the capillary, thus negative pressure being generated. As a result, the air gap of about 5 mm contributed to the prevention of reagent leakage, and with the capillary having an inner diameter of 50 µm, the volume of leakage could be reduced to about 0.6 nL. The system to generate negative pressure by using the microejector is very compact and simple, and is suitable for apparatuses for analyzing nucleic acids such as for examining genes on a small scale. An example of the constitution comprising a microejector is shown in FIG. 8(b). Herein, a microejector 1000 comprises a narrow tube 81 and a housing 82. The housing 82 is directly connected to the high pressure gas source via a solenoid valve 108 and a tube 810. Furthermore, the narrow tube 82 is connected to the exhaust slot of the group of solenoid valves 106 by the tube 811. When the gas flows from the high pressure gas source via the tube 810 into the housing 82, negative pressure is generated in the narrow tube 81, as described above, to suck the exhaust slot of the group of solenoid valves 106. The group of solenoid valves 106 are 3-way, as described above, and hence when the valves are OFF, the exhaust slot is directly connected to a group of tubes 105. Therefore, sucking the exhaust slot namely means sucking the air in the reagent vessels in the dispensing chip. Because the duration of sucking can be controlled by ON/OFF of the solenoid valve 108, the air in the reagent vessels can be sucked for desired duration. Accordingly, when the duration of sucking is suitably predetermined, a desired air gap can be formed at the tip of the capillary.

Figure 10:
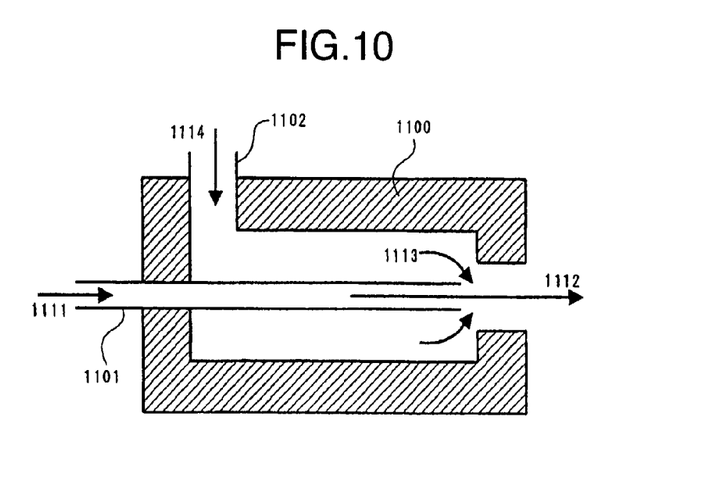
FIG. 10 shows another example of a sectional view of a microejector.

FIG. 10 shows another example of a sectional view of a microejector. It comprises a tube 1101, a housing 1100 and a tube 1102. The tube 1101 is connected to the high pressure gas source and the tube 1102 is connected to the regent vessels. When the high pressure gas flows into the microejector from a flow entrance like 1111 to an exhaust slot 1112, a flow like 1113 occurs in surroundings in the narrow tube end, and thereby the negative pressure is generated like 1114.

The problem of reagent leakage is very important in apparatuses analyzing nucleic acids. For example, in sequence analysis utilizing pyrosequencing, one of four nucleic acid substrates is dispensed, and whether extension occurs thereby or not is confirmed by luminescence; therefore, if a nucleic acid substrate different from the one of interest is intermixed, it directly becomes an analysis error. When evaluating a plurality of base sequences continuously, the analysis error exponentially increases with the number of sequences, so that the length of bases that can be analyzed is extremely limited. Therefore, reducing the volume of reagent leakage is an important objective. In the apparatus for analyzing nucleic acids in this embodiment, a reaction vessel uses about 20 μL of a sample solution. Compared with that, 0.6 nL corresponds to no more than 1/10000, and this is negligible. That is, by this constitution, the volume of leakage can be decreased to the negligible level.

Figure 4:
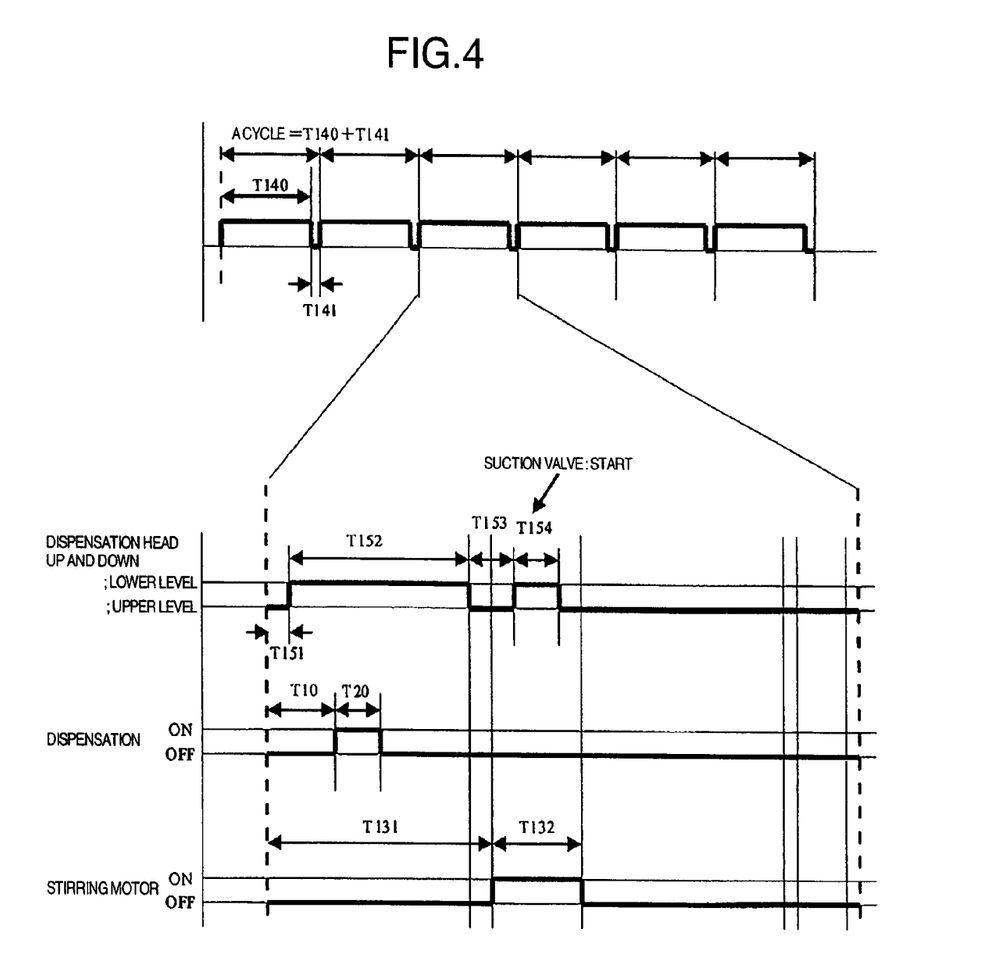
FIG. 4 illustrates a sequence to explain the operations of the apparatus at the time of measurement.
Figure 5:
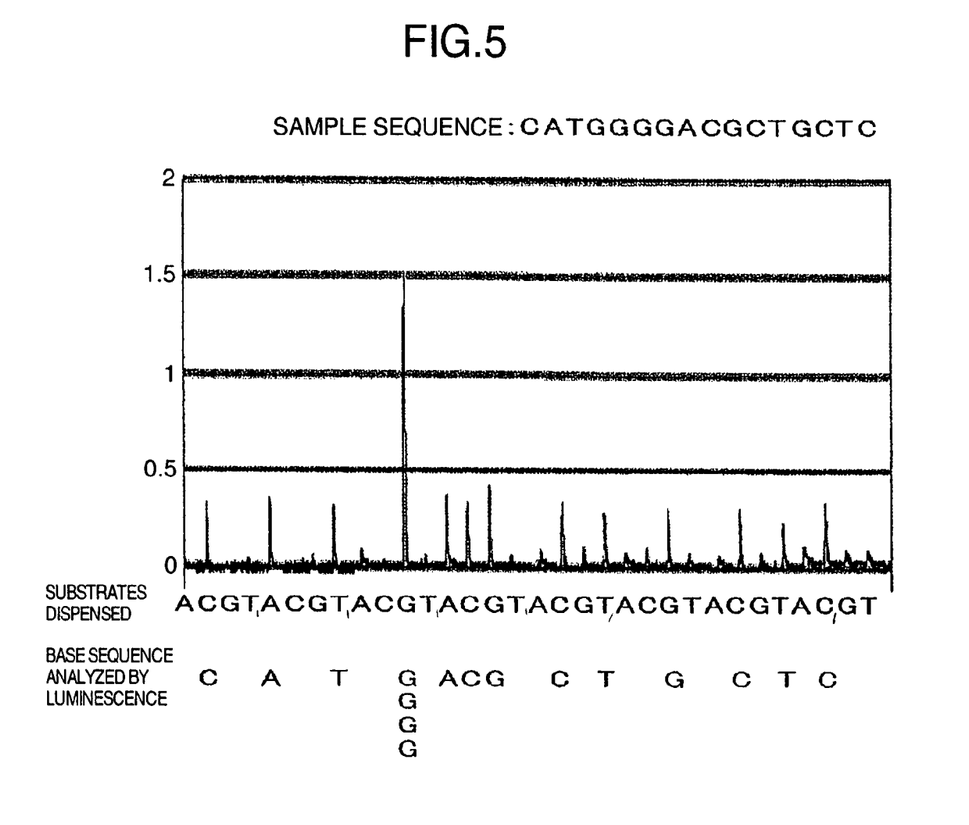
FIG. 5 illustrates the results of sequence analysis.

Next, the method for analyzing genes using the apparatus of this embodiment is described. FIG. 4 is an illustration of the time sequence of operations of the dispensing head, pressurization, and the vibration stirring motor, when one of the four dNTPs (i.e., dATPαS, dGTP, dCTP, and dTTP) is used as a reagent and is dispensed from the dispensing chip of this embodiment. The operations are as follows. First, the dispensing head is lowered so that the surface of the liquid in the reaction vessel becomes in contact with the tip of the capillary. Next, for the duration corresponding to a desired volume of the reagent to be dispensed, pressurization is performed by the high pressure gas to dispense the reagent. Then, the dispensing head is raised, and thereby the tip of the capillary is separated from the surface of the liquid in the reaction vessel. Finally, the stirring motor is operated for a predetermined period of stirring, and at the same time, sucking for negative pressure is performed for predetermined duration in order to form the air gap inside the capillary. For analyzing gene sequences, such series of operations can be repeated for every base. An example of the gene sequence analysis obtained in this embodiment is shown in FIG. 5. There, in FIG. 5, the substrates, A, G, C, and T refer to dATPαS, dGTP, dCTP, and dTTP, respectively. That is, an analogue of dATP is used for A, only. It is noted that the results of the analysis completely coincide with the base sequence of the sample SEQ ID1: CATGGGGACG CTGCTC, which has been already known.

Embodiment 2

Figure 6:
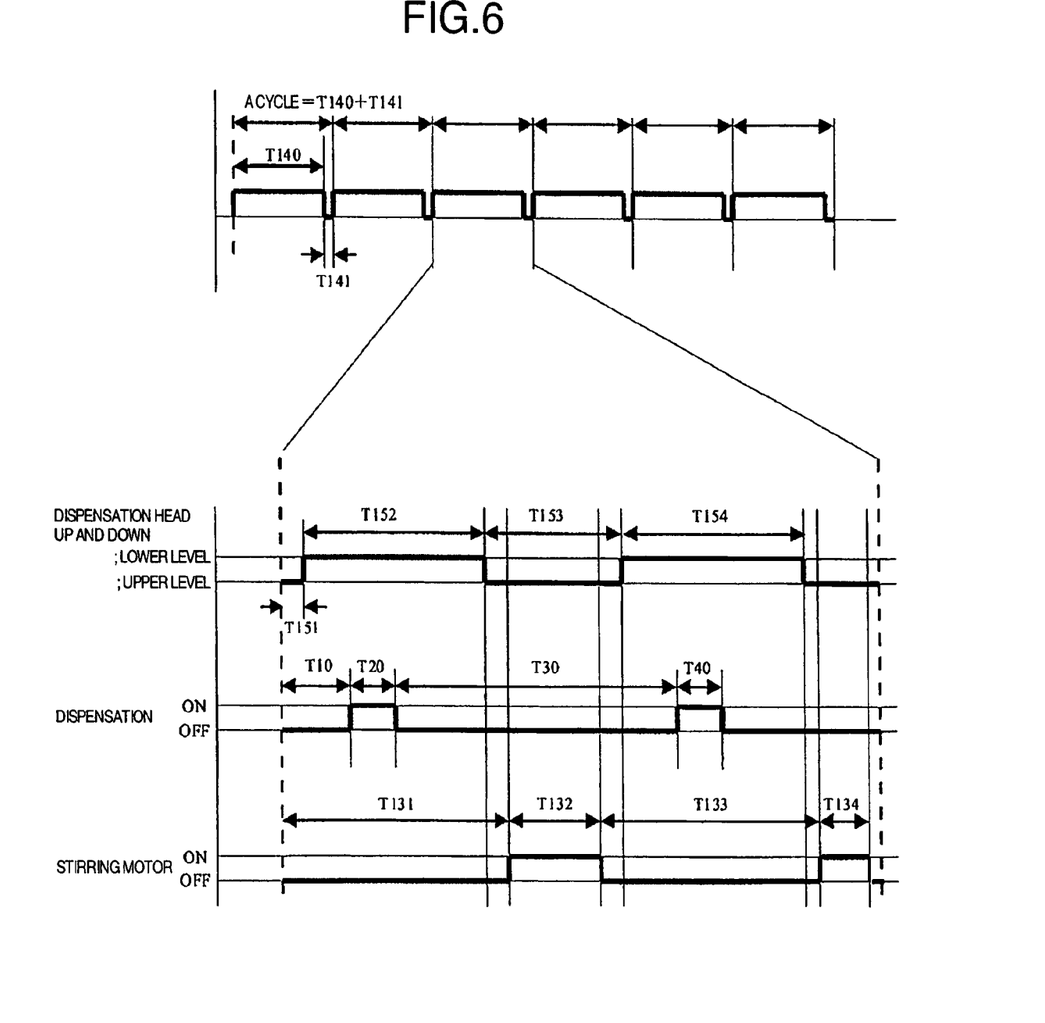
FIG. 6 illustrates a sequence of the operations of the apparatus at the time of measurement.
Figure 9:
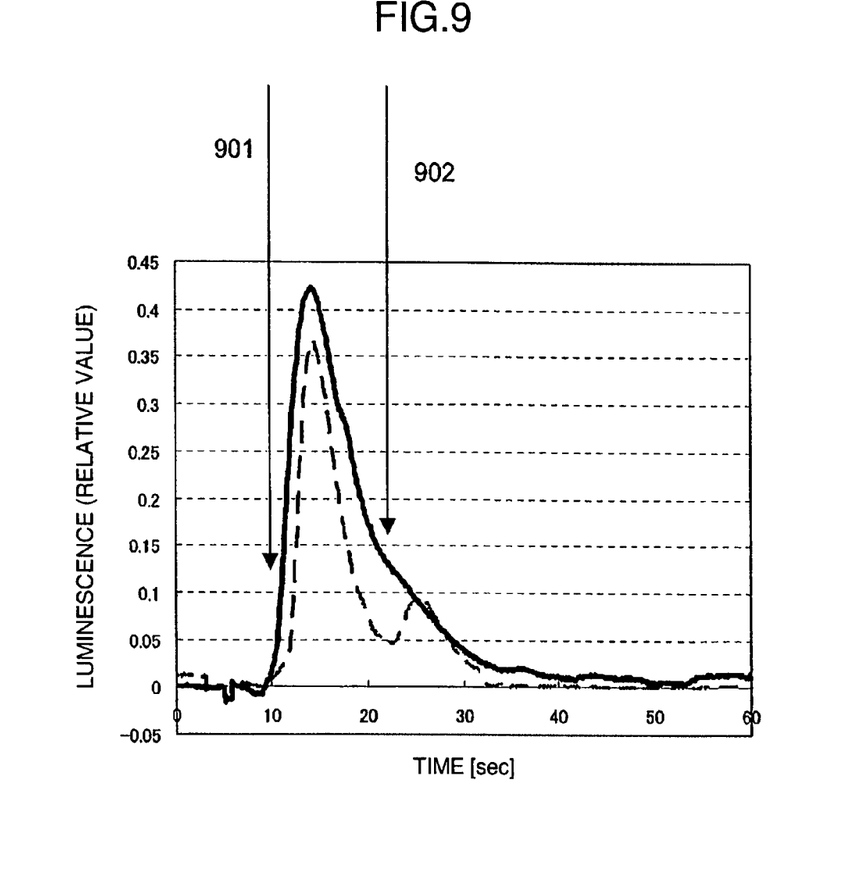
FIG. 9 illustrates the levels of luminescence when two different concentrations of the reagent are dispensed twice each.

Another embodiment related to dispensing reagents using the apparatus described in Embodiment 1 is described. First, when one substrate is dispensed, a lower concentration or a smaller volume of the reagent is preliminarily prepared and dispensed plural times. By using the present apparatus, such dispensing method can be readily realized. This is effective on occasions such that a concentration of the reagent is lowered in order to decrease leaking molecular weight, when the volume of leakage is about 0.6 nL, as described above; or that on continuous sequence analysis, a sequence continuously formed by the same base is observed, and thus the need of the additional reagent arises. In this embodiment, a case wherein dispensing is performed twice is described. FIG. 6 is an illustration of the time sequence of operations of the dispensing head, pressurization, and the vibration stirring motor, when one reagent is divided into two portions to dispense. When a single reagent is divided into two portions and dispensed, the emission following the first dispensing and the emission following the second dispensing are compared, and thereby whether the extension of the nucleic acid sample is completed or not can be determined. FIG. 9 is an example wherein by using different concentrations, dispensing was performed twice. The dashed line refers to the experiment using a ½ concentration of the concentration of the reagent dispensed in the experiment expressed by the solid line. In both experiments, dispensing was performed twice at 901 and 902. This figure indicates that when the injected reagent was sufficient, no emission was observed following the dispensing at 902, whereas with the ½ reagent concentration, components that had not reacted remained, so that further emission was observed following the second dispensing. This experimental example presents one example, and likewise, by injecting multiple times to obtain emission signals thereby, whether the reagent injected is sufficient or not can be determined.

This is effective to improve accuracy of sequence analysis, because an injecting amount of a reagent should be the optimum amount for the reaction. If the injecting amount is insufficient, nucleic acids that have not reacted will cause noises. On the other hand, when an excessive amount has been added and the next reagent is injected, the previous reagent that has not been completely degraded remains, resulting in a carry-over. A carry-over causes backward reading, etc., deteriorating measurement accuracy.

The optimum amount of a reagent varies with the number of bases extending. That is, when extending by two bases, the reagent twice in amount is required compared with when extending by one base. In many cases, the number of bases of the nucleic acid sequence of interest is unknown, and hence the number of bases extended by the injected reagent is not known. Thus, the optimum amount of the reagent can not be decided in advance. In such case, dispensing multiple times is effective.

Embodiment 3

Another embodiment related to the method of dispensing a plurality of reagents simultaneously using the apparatus described in Embodiment 1 is described.

In Embodiment 2, four substrates are dispensed one by one, but two, three, or all, i.e., two or more substrates can be optionally dispensed at the same time. It is important that the same dispensing chip that is used for usual sequence analysis can be used in such case as well. For example, in one of the techniques of analyzing polymorphism, in order to evaluate polymorphism at the extension probe side, polymorphism is allowed to be present at the 3'-terminal, wherein complementarity is analyzed. In this case, a mixture solution of four substrates is used as the reagent. Therefore, handling is different from normal reagents for sequence analysis, and a mixture solution of four substrates is particularly prepared for the polymorphism analysis. However, in the present apparatus, after sequence analysis is conducted, the same reagent dispensing tubes can be used only by changing samples in reaction vessels. Accordingly, various types of analysis can be simply attained.

In addition, when a known sequence is analyzed for confirmation and the possibility of heterogeneous SNPs is expected in advance, by dispensing such two bases simultaneously, a phase shift disadvantageously arising in pyrosequencing can be eliminated.

Embodiment 4

In regard to the dispensing chip described in Embodiment 1, another embodiment related to supplying measures to investigators is described. Herein, there is an example wherein simpler reagent management is provided for investigators as well as for suppliers. In the present invention, four nucleic acid substrates are used by injecting in the reagent vessel in the dispensing chip; four nucleic acid substrates can be added in this dispensing chip in advance, and sealed as it is and freeze-dried. If a reagent distributor seals and freeze-dries reagents in advance, investigators only have to load such already sealed dispensing chip into the dispensing head before experiment. The dispensing chip is not deteriorated by sterilization or freeze-drying, and the manufacturing cost is low. Therefore, dispensing chips designed to be disposable can significantly reduce possible experimental mistakes caused by the contamination of the reagents.

The present invention is utilized in apparatuses analyzing nucleic acids, which is a fundamental tool in life sciences and bioindustries, and, in particular, is applied in DNA sequence determination apparatuses and DNA examination apparatuses.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A reagent kit, comprising:
a single container; and
a first vessel, a second vessel, a third vessel and a fourth vessel, all said vessels disposed within the single container;
the first vessel containing a first liquid and comprising a first liquid delivering part, wherein the first liquid is deliverable from the first vessel through said first liquid delivery part;
the second vessel containing a second liquid and comprising a second liquid delivering part, wherein the second liquid is deliverable from the second vessel through said second liquid delivery part;
the third vessel containing a third liquid and comprising a third liquid delivering part, wherein the third liquid is deliverable from the third vessel through said third liquid delivery part; and
the fourth vessel containing a fourth liquid and comprising a fourth liquid delivering part, wherein the fourth liquid is deliverable from the fourth vessel through said fourth liquid delivery part,
wherein the first liquid delivering part, the second liquid delivering part, the third liquid delivering part, and the fourth liquid delivering part are positioned substantially concentrically and symmetrically with respect to a point, whereby each liquid delivering part is substantially equally spaced from the point,
the first liquid delivering part, the second liquid delivering part, the third liquid delivering part, and the fourth liquid delivering part each have a respective diameter equal to or greater than 25 μm and equal to or less than to 50 μm, and
wherein the first, second, third and fourth liquids comprise first, second, third and fourth different solutions, respectively.

2. The reagent kit according to claim 1, wherein each of said first liquid delivering part, said second liquid delivering part, said third liquid delivering part, and said fourth liquid delivering part is a capillary.

3. The reagent kit according to claim 1, wherein each of said first liquid, said second liquid, said third liquid, and said fourth liquid is freeze-dried.

4. The reagent kit according to claim 1, wherein said first, second, third, and fourth vessels have substantially cone-shaped connection parts to said first, second, third, and fourth liquid delivering parts, respectively, wherein each cone has an

SEQUENCE LISTING

```
<160> NUMBER OF SEQ ID NOS: 1

<210> SEQ ID NO 1
<211> LENGTH: 16
<212> TYPE: DNA
<213> ORGANISM: Artificial Sequence
<220> FEATURE:
<223> OTHER INFORMATION: chemically synthesized

<400> SEQUENCE: 1
catggggacg ctgctc                                                    16
``` apex at the point where each of said first, second, third and fourth liquid delivering parts is positioned.

5. A kit according to claim 1, wherein the first liquid, second liquid, third liquid and fourth liquid are each dATP, dCTP, dTTP and dGTP, respectively, different solutions or at least one of the first liquid, second liquid, third liquid and fourth liquid is analogue of dNTP.

6. A kit according to claim 5, wherein the analogue of dNTP is dNTPαS.

7. A kit according to claim 1, wherein combinations of the first vessel, second vessel, third vessel and fourth vessel, with the corresponding first liquid delivering part, second liquid delivering part, third liquid delivering part and fourth liquid delivering part are positioned substantially concentrically with a diameter of 9 mm or less and symmetrically with respect to a point.

8. The kit according to claim 1, wherein the single container has a pin for positioning.

9. The kit according to claim 1, wherein an end of a top of the first, second, third and fourth vessels is essentially on the same plane.

10. The reagent kit of claim 1, wherein the first, second, third and fourth solutions comprise four respective different reagents.

11. A reagent kit, comprising:
a single container;
a first vessel, a second vessel, a third vessel and a fourth vessel, all said vessels disposed within the single container;
the first vessel containing a first liquid and comprising a first liquid delivering part, wherein the first liquid is deliverable from the first vessel through said first liquid delivery part;
the second vessel containing a second liquid and comprising a second liquid delivering part from which said second liquid is delivered, wherein the second liquid is deliverable from the second vessel through said second liquid delivery part;
the third vessel containing a third liquid and comprising a third liquid delivering part from which said third liquid is delivered, wherein the third liquid is deliverable from the third vessel through said third liquid delivery part; and
the fourth vessel containing a fourth liquid and comprising a fourth liquid delivering part from which said fourth liquid is delivered, wherein the fourth liquid is deliverable from the fourth vessel through said fourth liquid delivery part,
wherein the first liquid delivering part, the second liquid delivering part, the third liquid delivering part, and the fourth liquid delivering part are positioned substantially concentrically and symmetrically with respect to a point, whereby each liquid delivering part is substantially equally spaced from the point,
the first liquid delivering part, the second liquid delivering part, the third liquid delivering part, and the fourth liquid delivering part each have a respective diameter equal to or greater than 25 μm and equal to or less than to 50 μm; and an ejector operatively associated with the first, second, third and fourth vessels for selectively dispensing the respective first, second, third and fourth liquids from the first, second, third and fourth vessels, respectively.

12. The reagent kit of claim 11, wherein the ejector comprises a pressure generating device for selecting applying pressure to said first, second, third and fourth vessels, thereby dispensing the respective first, second, third and fourth liquids from the first, second, third and fourth vessels, respectively.

13. The reagent kit of claim 12, wherein the pressure generative device comprises at least on solenoid for controlling which one or ones of the first, second, third and fourth vessels are pressurized to thereby dispense the respective liquid contained therein.

* * * * *